(12) United States Patent
Park

(10) Patent No.: US 8,782,820 B2
(45) Date of Patent: Jul. 22, 2014

(54) GOGGLES WITH FILM WINDING MECHANISM

(75) Inventor: Chun-bae Park, Gimhae-si (KR)

(73) Assignee: Kyungdo Co., Ltd. (KR)

( * ) Notice: Subject to any disclaimer, the term of this patent is extended or adjusted under 35 U.S.C. 154(b) by 324 days.

(21) Appl. No.: 13/303,288

(22) Filed: Nov. 23, 2011

(65) Prior Publication Data

US 2013/0047324 A1    Feb. 28, 2013

(30) Foreign Application Priority Data

Aug. 30, 2011   (KR) ........................ 10-2011-0086874

(51) Int. Cl.
   *A61F 9/02*    (2006.01)
(52) U.S. Cl.
   USPC ................................................ 2/438; 351/41
(58) Field of Classification Search
   USPC ........... 2/424, 9, 15, 206, 422, 434, 432, 438, 2/436, 435
   See application file for complete search history.

(56) References Cited

U.S. PATENT DOCUMENTS

| 4,528,701 | A | * | 7/1985 | Smith | 2/438 |
| 4,748,697 | A | * | 6/1988 | Hodnett | 2/438 |
| 5,203,035 | A | * | 4/1993 | Lawlor | 2/438 |
| 6,415,452 | B1 | * | 7/2002 | Watanabe et al. | 2/438 |
| 6,416,177 | B1 | * | 7/2002 | Gibson | 351/41 |

\* cited by examiner

*Primary Examiner* — Katherine Moran

(74) *Attorney, Agent, or Firm* — Park & Associates IP Law, P.C.

(57) ABSTRACT

Disclosed herein are industrial goggles. The goggles include a main body having protective glass and formed to correspond to a curvature of a face. A cover is hinged to one side of the front of the main body. A film unwinding roll has a film thereon. An unwinding-roll holding part vertically holds the film unwinding roll on one side of the main body and includes a stationary locking step, a movable locking step, and an elastic spring. A film winding shaft is provided vertically on the other side of the main body to wind the film from the film unwinding roll. A film feeding lever is coupled to the film winding shaft in a gear coupling manner and hinged to the main body. A ratchet means prevents the film feeding lever from rotating in a reverse direction. An elastic support member supports the main body against the face.

5 Claims, 5 Drawing Sheets

GOGGLES WITH FILM WINDING MECHANISM

REFERENCE TO RELATED APPLICATIONS

This application claims the priority benefit of Korean Patent Application No. 10-2011-0086874 filed on Aug. 30, 2011, the entire contents of which are incorporated herein by reference.

FIELD OF THE INVENTION

The present invention relates generally to goggles and, more particularly, to industrial or utility goggles, capable of protecting protective glass of the goggles using a film, in which the film can be rapidly replaced with a new one when the film is soiled.

BACKGROUND OF THE INVENTION

Industrial goggles are worn close to a worker's face when performing painting, sanding, and welding work to protect the worker's eyes.

Industrial goggles are generally constructed so that protective glass is provided on the front of the goggles and they are held on the head by an elastic band. Unlike leisure goggles, most industrial goggles are equipped with a protective hood.

Industrial goggles are disclosed in Korean Patent Appl. No. 10-2006-0026214 that is entitled "industrial goggles and protective hood having the same", Korean Patent Appl. No. 10-2005-0093682, etc.

However, a problem with conventional industrial goggles is that a worker must clean the protective glass whenever the protective glass becomes dirty. Moreover, when the contamination of the protective glass is serious, the protective glass should be replaced with a new one or the goggles themselves should be replaced with new ones so as to ensure a worker's vision.

In order to solve the problems, there has been proposed a configuration wherein a film is disposed on the front of the protective glass and moves from one side to the other side in order to protect the protective glass.

However, a problem with such industrial goggles is that the use of a motor causes frequent failures, so that it is difficult to move the film by the desired distance and thereby the film must be frequently replaced with a new one.

SUMMARY OF THE INVENTION

Accordingly, the present invention has been made keeping in mind the above problems occurring in the prior art, and an object of the present invention is to provide industrial goggles, capable of rapidly moving a film by the desired distance, when the film disposed on the front of protective glass to protect the protective glass is soiled.

Another object of the present invention is to provide industrial goggles, capable of moving a film because it has a simple structure.

In order to accomplish the above objects, the present invention provides industrial goggles, including a main body having on a front thereof protective glass and formed to correspond to a curvature of a worker's face; a cover hinged to one side of the front of the main body; a cylindrical film unwinding roll around which a film is wound; an unwinding-roll holding part vertically holding the film unwinding roll on one side of the main body in such a way that the film unwinding roll rotates, the unwinding-roll holding part having a stationary locking step protruding into the main body, a movable locking step movably coupled to a position opposite the stationary locking step, and an elastic spring elastically supporting the movable locking step; a film winding shaft provided vertically on the other side of the main body to wind the film from the film unwinding roll; a film feeding lever coupled to the film winding shaft in a gear coupling manner, and hinged to the main body; a ratchet means preventing the film feeding lever from rotating in a reverse direction; and an elastic support member coupled to both side ends of the main body, thus supporting the main body against the worker's face.

The film feeding lever may include a rotating shaft provided adjacent to the film winding shaft, a driving gear provided on an end of the rotating shaft, a driven gear coupled to the film winding shaft and engaging with the driving gear, and a handle extending from the rotating shaft in such a way as to protrude outwards.

Further, the rotating shaft may be installed in the main body using a torsion coil spring.

Furthermore, a face contact member made of a silicone material may be coupled to a rear of the main body, thus allowing the main body to come in close contact with the face, and the face contact member may comprise a bendable portion that has continuous ridges and furrows.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE INVENTION

Hereinafter, the preferred embodiments of the present invention will be described in detail with reference to the accompanying drawings.

Figure 1:
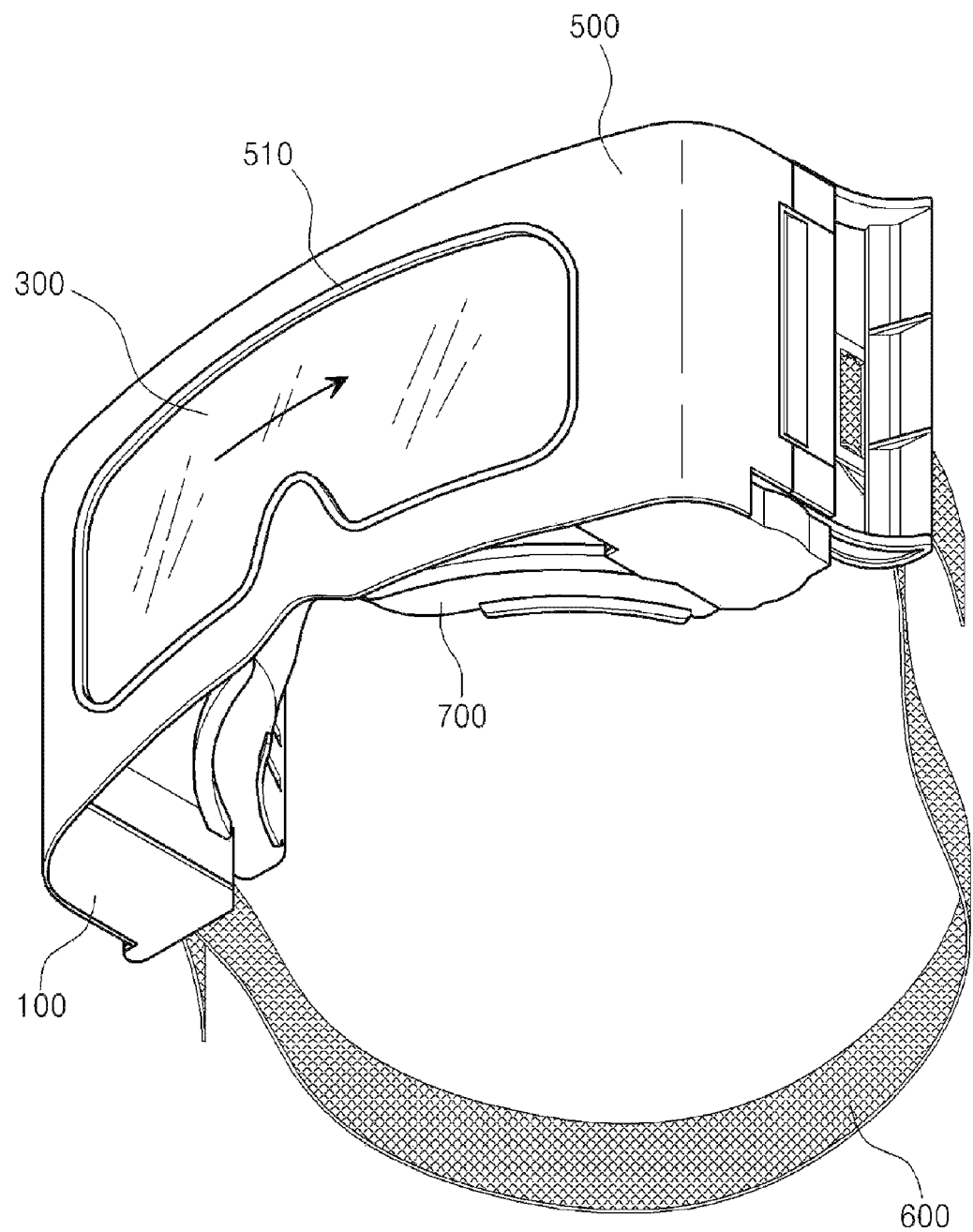
FIG. 1 is a perspective view illustrating industrial goggles in accordance with a preferred embodiment of the present invention.

FIG. 1 is a perspective view illustrating industrial goggles in accordance with a preferred embodiment of the present invention.

As shown in FIG. 1, the industrial goggles according to the present invention include a main body 100 that defines a basic frame. On the front of the main body 100 there is protective glass which is formed to correspond to the curvature of a worker's face. A face contact member 700 is coupled to a rear of the main body 100 to allow the main body 100 to come in close contact with the face. A cover 500 is hinged to one side of the front of the main body 100.

Here, the main body 100 is formed to completely surround a worker's eye area. The face contact member 700 separates the worker's eye area and the rear of the main body 100 from each other by a predetermined distance.

Further, an elastic support member 600 is coupled to both side ends of the main body 100 to support the main body 100 against the worker's face. The elastic support member 600 comprising a rubber band is fitted into coupling holes which are formed in both side ends of the main body 100, and its length is adjusted to fit the worker's head.

As shown in FIG. 1, a film 300 is exposed to the outside through an opening 510 formed in the cover 500 in the shape of sunglasses. Protective glass 200 is located inside the film 300.

Figure 2:
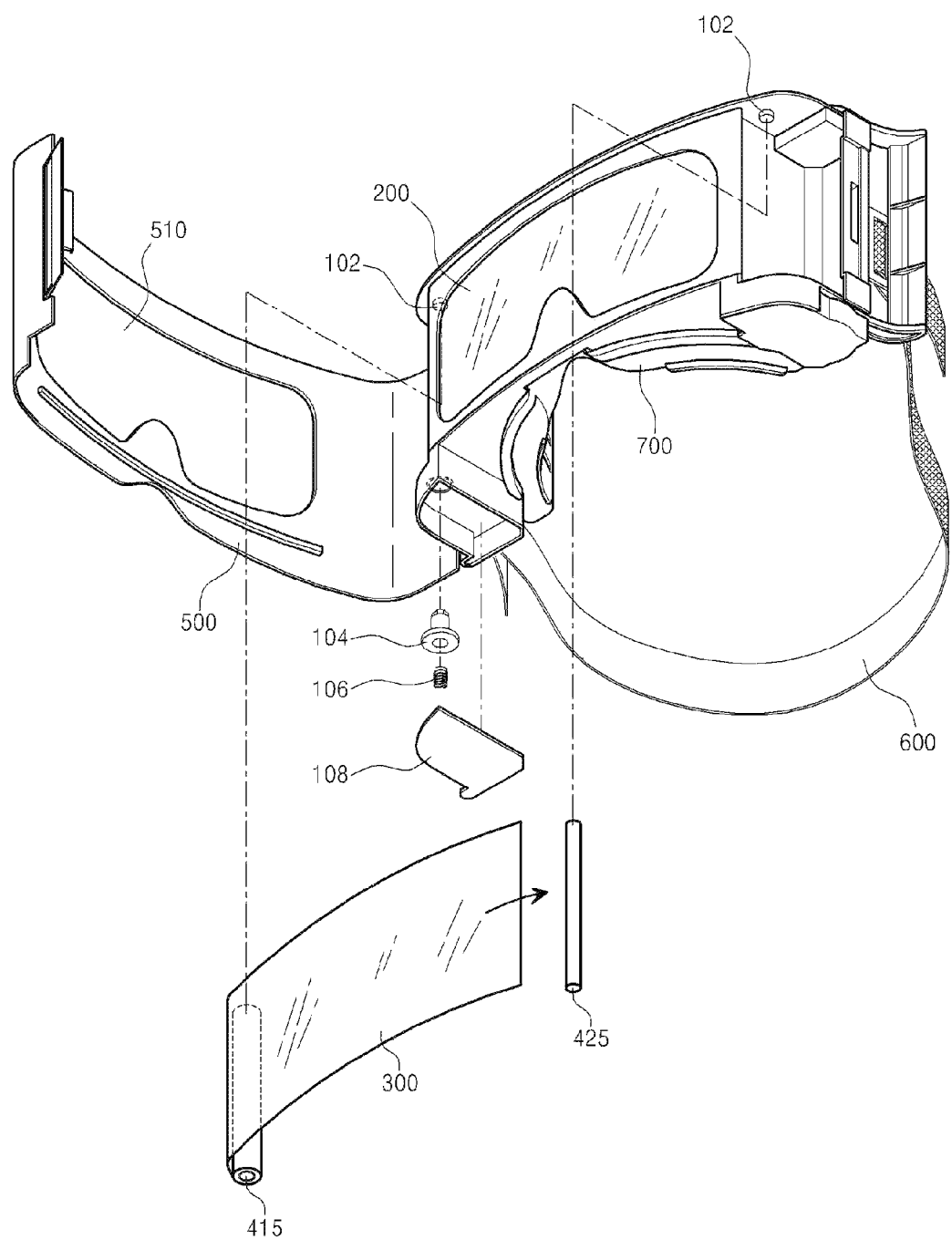
FIG. 2 is a view illustrating the industrial goggles of FIG. 1, when a cover is open.

FIG. 2 is a view illustrating the industrial goggles of FIG. 1, when the cover is open.

As shown in FIG. 2, when the cover 500 of the industrial goggles according to the present invention is opened, a cylindrical film unwinding roll 415 around which the film 300 is wound may be secured to one side of the main body 100.

The film unwinding roll 415 is vertically held on one side of the main body 100 via an unwinding-roll holding part in such a way as to rotate. The unwinding-roll holding part includes a stationary locking step 102 protruding into the main body 100, a movable locking step 104 movably coupled to a position opposite the stationary locking step 102, and an elastic spring 106 elastically supporting the movable locking step 104.

Further, the movable locking step 104 and the elastic spring 106 are accommodated in the main body 100 by a locking step cover 108.

The film 300 unwound from the film unwinding roll 415 is wound around a film winding shaft 425 that is vertically installed at the other side of the main body 100. The protective glass 200 provided on the front of the main body 100 is protected by the film 300 without being exposed to the outside.

Particularly, the film unwinding roll 415 is manufactured as consumables. Thus, if the film 300 is used up, the film unwinding roll 415 may be rapidly replaced with another film unwinding roll.

The protective glass 200 is held by a glass holding part, and is made of a transparent plastic material. Preferably, the protective glass 200 is made of acryl, which is light and has superior processability. Preferably, the protective glass 200 is also manufactured to be replaced with a new one, when the protective glass 200 has been used for a lengthy period of time and has become soiled.

Figure 3:
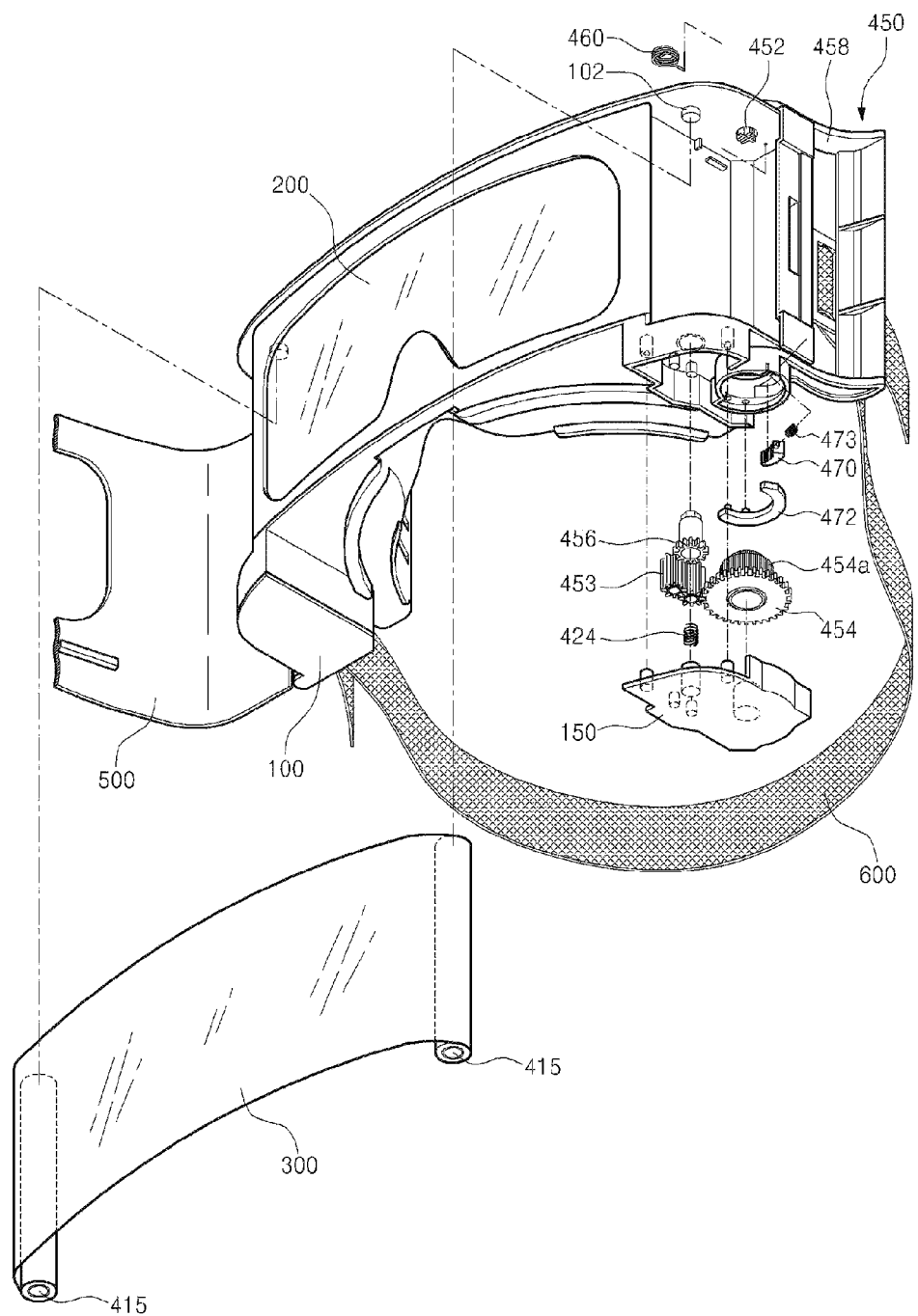
FIG. 3 is an exploded perspective view illustrating the industrial goggles in accordance with the preferred embodiment of the present invention.

FIG. 3 is an exploded perspective view illustrating the industrial goggles in accordance with the preferred embodiment of the present invention.

Similarly to the film unwinding roll 415, the film winding shaft 425 is coupled to the main body 100 by a stationary locking step 102 and a movable locking step 104. The movable locking step for locking the film winding shaft 425 is provided with a driven gear 456.

Next, a film feeding lever will be described.

The film feeding lever 450 is coupled to the film winding shaft 425 in a gear coupling manner, and is hinged to the main body 100.

To be more specific, the film feeding lever 450 includes a rotating shaft 452, a driving gear 454, a driven gear 456, a handle 458, and an elastic spring 424 installed in a cover 150 to bias the driven gear 456 upwardly. The rotating shaft 452 is provided adjacent to the film winding shaft 425. The driving gear 454 is provided on an end of the rotating shaft 452. The driven gear 456 is coupled to the film winding shaft 425 and engages with the driving gear 454. The handle 458 extends from the rotating shaft 452 in such a way as to protrude outwards.

Thus, if the worker rotates the protruding handle 456, the driven gear 456 is rotated by the driving gear 454, thus rotating the film winding shaft 425 and moving the film 300.

The industrial goggles further include a ratchet means to prevent the film feeding lever 450 from rotating in a reverse direction.

The ratchet means prevents the film winding shaft 425 from rotating when the film feeding lever 450 returns to its original position using the handle 458. The ratchet means includes a ratchet pawl 470, a spring 473 biasing the ratchet pawl 470 in one direction, and a ratchet cover 472 supporting the ratchet means. A ratchet wheel 454a coming in contact with the ratchet pawl 470 is provided on the driving gear 454.

Here, the rotating shaft 452 of the film feeding lever 450 may be installed in the main body 100 using a torsion coil spring 460. Thus, when the worker has moved the film 300 by a predetermined distance and releases the handle 458, the film 300 automatically returns to its original position, and the reverse rotation of the film winding shaft 425 is prevented by the ratchet means. One end of the torsion coil spring 460 is secured to the main body 100, while the other end is secured to the rotating shaft.

Further, an idle gear 453 is provided between the driving gear 454 and the driven gear 456 to control the rotating angle of the film feeding lever 450 and the moving speed of the film 300.

Another embodiment according to the present invention will be described below.

Figure 4:
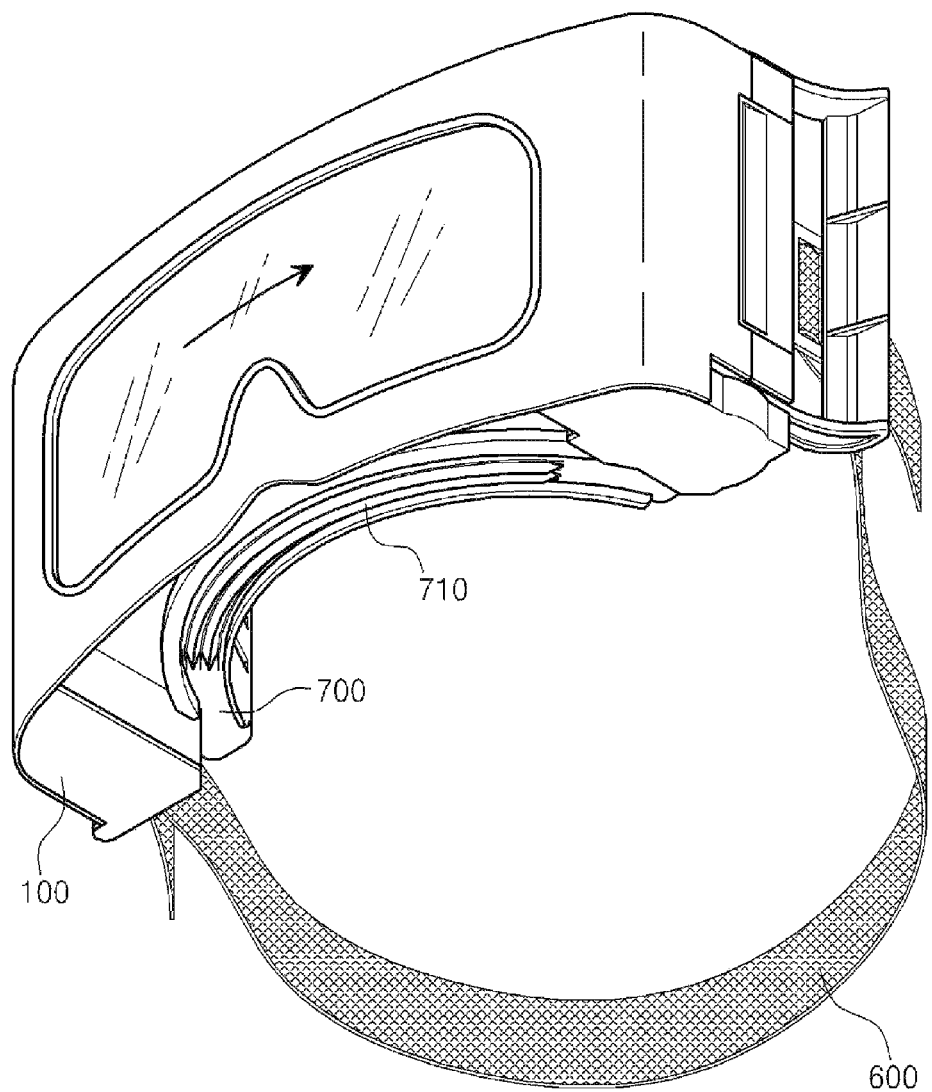
FIG. 4 is an exploded perspective view illustrating industrial goggles in accordance with another preferred embodiment of the present invention.
Figure 5:
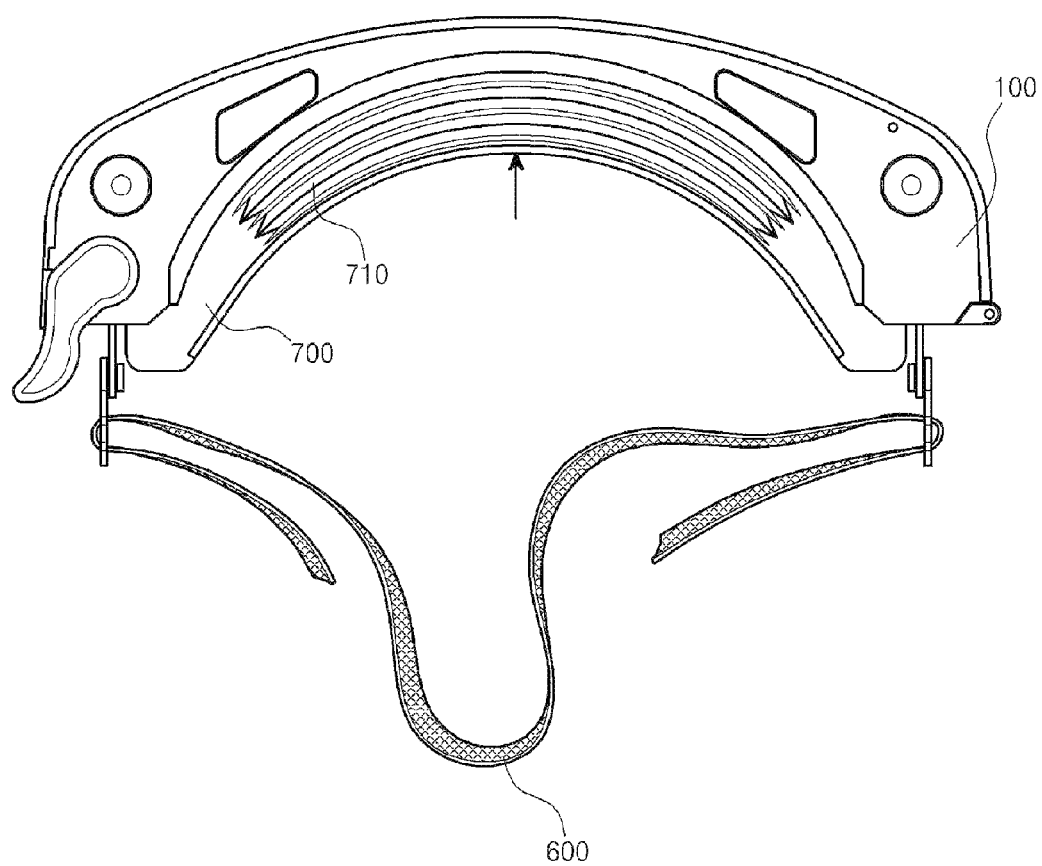
FIG. 5 is a plan view of FIG. 4.

FIG. 4 is an exploded perspective view illustrating industrial goggles in accordance with another preferred embodiment of the present invention, and FIG. 5 is a plan view of FIG. 4.

As shown in FIG. 4, a face contact member 700 made of a silicone material is coupled to a rear of a main body 100 to allow the main body 100 to come in close contact with the face. In order to enhance close contact ability, the face contact member 700 is provided with a bendable portion 710 that has continuous ridges and furrows.

The bendable portion 710 has a corrugated shape, and may be elastically compressed to a greater extent when pushed in the direction shown by the arrow of FIG. 5.

The main technical concept of the present invention is to provide industrial goggles, capable of conveniently moving a soiled film. Since the above embodiments described with reference to the accompanying drawings are merely illustrative, the scope of the invention is to be determined solely by the appended claims.

As described above, the present invention provides industrial goggles, configured such that a film can be moved by a desired length using a film feeding lever, thus providing a clear view for a worker, therefore improving work efficiency and reducing a goggle replacing cost incurred by the replacement of protective glass.

Further, the present invention provides industrial goggles, capable of improving the sensation when worn using a face contact member made of a silicone material.

What is claimed is:

1. A goggle comprising:
   a main body having a protective glass coupled thereto;
   a cover hinged to one side of of the main body;
   a film unwinding roll having a film wound there-around, the film unwinding roll placed vertically at a lateral side of the main body and behind the cover;
   a stationary locking step affixed to the main body and having a downwardly extending post portion;
   a movable locking step movably coupled to the main body opposite from the stationary locking step, the movable locking step having an upwardly extending post portion, said post portion of the stationary locking step and said post portion of the movable locking step being aligned coaxially to each other and having the film unwinding roll rotatably coupled thereto;

an elastic spring elastically supporting the movable locking step to bias toward the stationary locking step;

a film winding shaft provided vertically on another lateral side of the main body opposite from the film unwinding roll to wind the film from the film unwinding roll;

a film feeding lever coupled to the film winding shaft and hinged to the main body, said film feeding lever having a plurality of gears coupled thereto to rotate the film winding shaft and wind the film on the film winding shaft;

ratchet means coupled to the plurality of gears for preventing the film feeding lever from rotating in a reverse direction; and an elastic support member coupled to both side ends of the main body to secure the main body onto the worker's face.

2. The goggle as set forth in claim 1, wherein the film feeding lever comprises a rotating shaft provided adjacent to the film winding shaft, and a handle extending laterally from the rotating shaft, and wherein the plurality of gears comprises a driving gear provided on an end of the rotating shaft, and a driven gear coupled to the film winding shaft and engaging with the driving gear.

3. The goggle as set forth in claim 2, wherein the rotating shaft is installed in the main body using a torsion coil spring.

4. The goggle as set forth in claim 1, wherein a face contact member made of a silicone material is coupled to a rear side of the main body, allowing the main body to come in close contact with the face.

5. The goggle as set forth in claim 4, wherein the face contact member comprises a bendable portion that has continuous ridges and furrows.

* * * * *